United States Patent [19]

Barth

[11] 4,276,285
[45] * Jun. 30, 1981

[54] COMBINATIONS OF PENICILLANIC ACID 1,1-DIOXIDE WITH 7-(D-2-[4-ETHYLPIPERAZIN-2,3-DIONE-1-CARBOXAMIDO]-2-[4-HYDROXYPHENYL-]ACETAMIDO)-3-([1-METHYL-5-TETRAZOLYL]THIOMETHYL)-3-DESACETOX-YMETHYLCEPHALOSPORANIC ACID

[75] Inventor: Wayne E. Barth, East Lyme, Conn.

[73] Assignee: Pfizer Inc., New York, N.Y.

[*] Notice: The portion of the term of this patent subsequent to Nov. 18, 1987, has been disclaimed.

[21] Appl. No.: 17,807

[22] Filed: Mar. 5, 1979

Related U.S. Application Data

[63] Continuation-in-part of Ser. No. 963,763, Nov. 27, 1978, abandoned, which is a continuation-in-part of Ser. No. 890,451, Mar. 29, 1978, abandoned, which is a continuation-in-part of Ser. No. 879,381, Feb. 21, 1978, abandoned, which is a continuation-in-part of Ser. No. 804,320, Jun. 7, 1977, abandoned.

[51] Int. Cl.$^3$ ............................................. H61K 35/00
[52] U.S. Cl. .................................................... 424/114
[58] Field of Search ......................................... 424/114

[56] References Cited

U.S. PATENT DOCUMENTS

| | | | |
|---|---|---|---|
| 3,197,466 | 7/1965 | Chow et al. | 260/239.1 |
| 3,536,698 | 10/1970 | Chauvette et al. | 260/239.1 |

FOREIGN PATENT DOCUMENTS 1072108  5/1964  United Kingdom ................ 260/237.1

OTHER PUBLICATIONS

Guddal et al., Tetrahedron Letters, No. 9, 381, (1962).
Harrison et al., J. Chem. Soc., (London), Perkin I, 1977, (1976).
Antibiotiki, 73, pp. 155–158, (1967).
Chemical Abstracts 88:22943d, (1978), Abstracting S. African Pat. No. 7600296 Published 11-16-76.
Busson et al., "Recent Advances in the Chemistry of B–Lactan Antibiotics," J. Elka, Ed., Burlington House, London, 1977, Chapter 32, pp. 304–313.

*Primary Examiner*—Jerome D. Goldberg
*Attorney, Agent, or Firm*—Connolly and Hutz

[57] ABSTRACT

Penicillanic acid 1,1-dioxide, pharmaceutically-acceptable salts thereof, and esters thereof readily hydrolyzable in vivo, enhance the antibacterial effectiveness of 7-(D-2-[4-ethylpiperazin-2,3-dione-1-carboxamido]-2-[4-hydroxyphenyl]acetamido)-3-([1-methyl-5-tetrazolyl]thiomethyl)-3-desacetoxymethylcephalosporanic acid, and salts thereof, against many beta-lactamase producing bacteria.

9 Claims, No Drawings

COMBINATIONS OF PENICILLANIC ACID 1,1-DIOXIDE WITH 7-(D-2-[4-ETHYLPIPERAZIN-2,3-DIONE-1-CARBOXAMIDO]-2-[4-HYDROXYPHENYL-]ACETAMIDO)-3-([1-METHYL-5-TETRAZOLYL]-THIOMETHYL)-3-DESACETOXYMETHYLCEPHALOSPORANIC ACID

CROSS-REFERENCE TO RELATED APPLICATIONS

This application is a continuation-in-part of application Ser. No. 963,763, filed Nov. 27, 1978 and now abandoned, which is a continuation-in-part of application Ser. No. 890,451, filed Mar. 29, 1978 and now abandoned, which is a continuation-in-part of application Ser. No. 879,381, filed Feb. 21, 1978, and now abandoned, which in turn is a continuation-in-part of application Ser. No. 804,320, filed June 7, 1977, and now abandoned.

BACKGROUND OF THE INVENTION

One of the most well-known and widely used of the classes of antibacterial agents is the class known as the beta-lactam antibiotics. These compounds are characterized in that they have a nucleus consisting of a 2-azetidinone (beta-lactam) ring fused to either a thiazolidine or a dihydro-1,3-thiazine ring. When the nucleus contains a thiazolidine ring, the compounds are usually referred to generically as penicillins, whereas when the nucleus contains a dihydrothiazine ring, the compounds are referred to as cephalosporins. Typical examples of penicillins which are commonly used in clinical practice are benzylpenicillin (penicillin G), phenoxymethylpenicillin (penicillin V), ampicillin and carbenicillin; typical examples of common cephalosporins are cephalothin, cephalexin and cefazolin.

However, despite the wide use and wide acceptance of the beta-lactam antibiotics as valuable chemotherapeutic agents, they suffer from the major drawback that certain members are not active against certain microorganisms. It is thought that in many instances this resistance of a particular microorganism to a given beta-lactam antibiotic results because the microorganism produces a beta-lactamase. The latter substances are enzymes which cleave the beta-lactam ring of penicillins and cephalosporins to give products which are devoid of antibacterial activity. However, certain substances have the ability to inhibit beta-lactamases, and when a beta-lactamase inhibitor is used in combination with a penicillin or cephalosporin it can increase or enhance the antibacterial effectiveness of the penicillin or cephalosporin against certain microorganisms. It is considered that there is an enhancement of antibacterial effectiveness when the antibacterial activity of a combination of a beta-lactamase inhibiting substance and a beta-lactam antibiotic is significantly greater than the sum of the antibacterial activities of the individual components.

Penicillanic acid 1,1-dioxide, its pharmaceutically-acceptable salts, and its esters readily hydrolyzable in vivo are potent inhibitors of microbial beta-lactamases. According to this invention there is provided a method for increasing the effectiveness of the cephalosporin antibiotic, 7-(D-2-[4-ethylpiperazin-2,3-dione-1-carboxamido]-2-[4-hydroxyphenyl]-acetamido)-3-([1-methyl-5-tetrazolyl]thiomethyl)-3-desacetoxymethylcephalosporanic acid and its pharmaceutically-acceptable salts, using said penicillanic acid 1,1-dioxide, pharmaceutically acceptable salts thereof, or esters thereof readily hydrolyzable in vivo. Additionally, according to this invention, there are provided pharmaceutical compositions, useful for treating bacterial infections in mammals, which comprise penicillanic acid 1,1-dioxide or a pharmaceutically acceptable salt thereof or an ester thereof readily hydrolyzable in vivo, and 7-(D-2-[4-ethylpiperazin-2,3-dione-1-carboxamido]-2-[4-hydroxyphenyl]acetamido)-3-([1-methyl-5-tetrazolyl]thiomethyl)-3-desacetoxymethylcephalosporanic acid or a pharmaceutically-acceptable salt thereof.

1,1-Dioxides of benzylpenicillin, phenoxymethylpenicillin and certain esters thereof have been disclosed in U.S. Pat. No. 3,197,466 and No. 3,536,698, and in an article by Guddal et al., in *Tetrahedron Letters,* No 9, 381 (1962). Harrison et al., in the *Journal of the Chemical Society* (London), Perkin I, 1772 (1976), have disclosed a variety of penicillin 1,1-dioxides and 1-oxides, including methyl phthalimidopenicillanate 1,1-dioxide, methyl 6,6-dibromopenicillanate 1,1-dioxide, methyl penicillanate 1-alpha-oxide, methyl penicillanate 1-beta-oxide, 6,6-dibromopenicillanic acid 1-alpha-oxide and 6,6-dibromopenicillanic acid 1-beta-oxide.

SUMMARY OF THE INVENTION

According to the invention, there is provided a method of increasing the effectiveness of the beta-lactam antibiotic, 7-(D-2-[4-ethylpiperazin-2,3-dione-1-carboxamido]-2-[4-hydroxyphenyl]acetamido)-3-([1-methyl-5-tetrazolyl]thiomethyl)-3-desacetoxymethylcephalosporanic acid, and the pharmaceutically-acceptable salts thereof, in a mammalian subject. Said method comprises co-administering to said subject a beta-lactam antibiotic effectiveness increasing amount of a compound of the formula

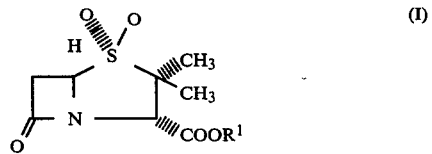

or a pharmaceutically-acceptable base salt thereof, wherein $R^1$ is selected from the group consisting of hydrogen and ester-forming residues readily hydrolyzable in vivo.

Also, according to the invention, there are provided pharmaceutical compositions, useful for treating bacterial infections in mammals. Said compositions comprise 7-(D-2-[4-ethylpiperazin-2,3-dione-1-carboxamido]-2-[4-hydroxyphenyl]acetamido)-3-([1-methyl-5-tetrazolyl]thiomethyl)-3-desacetoxymethylcephalosporanic acid or a pharmaceutically-acceptable salt thereof, and a compound of the formula I or a pharmaceutically-acceptable base salt thereof, wherein $R^1$ is as defined previously.

The term "ester-forming residues readily hydrolyzable in vivo" is here intended to refer to non-toxic ester residues which are rapidly cleaved in mammalian blood or tissue, to release the corresponding free acid (i.e. the compound of formula I, wherein $R^1$ is hydrogen). Typical examples of such readily hydrolyzable ester-forming residues which can be used for $R^1$ are alkanoyloxymethyl having from 3 to 8 carbon atoms, 1-(alkanoyloxy)ethyl having from 4 to 9 carbon atoms, 1-methyl-1-(alkanoyloxy)-ethyl having from 5 to 10 carbon aftoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-[alkoxycarbonyl]amino)ethyl having from 4 to 10 carbon atoms, 3-phthalidyl, 4-crotonolactonyl and gamma-butyrolacton-4-yl.

DETAILED DESCRIPTION OF THE INVENTION

This invention relates to the compounds of formula I, and throughout this specification, they are referred to as derivatives of pencillanic acid, which is represented by the structural formula

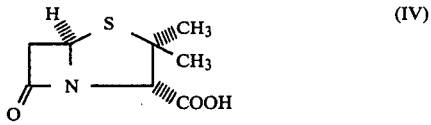
(IV)

In formula IV, broken line attachment of a substituent to the bicyclic nucleus indicates that the substituent is below the plane of the bicyclic nucleus. Such a substituent is said to be in the α-configuration. Conversely, solid line attachment of a substituent to the bicyclic nucleus indicates that the substituent is attached above the plane of the nucleus. This latter configuration is referred to as the β-configuration.

Also in this specification reference is made to a derivative of cephalosporanic acid. Cephalosporanic acid has the formula

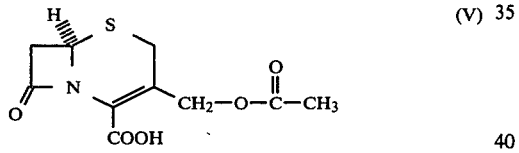
(V)

In formula V, the hydrogen at C-6 is below the plane of the bicyclic nucleus. The derived term 3-desacetoxymethylcephalosporanic acid refers to the structure VI.

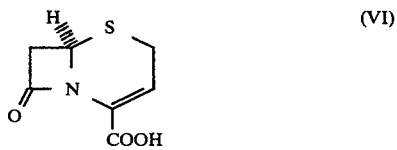
(VI)

4-Crotonolactonyl and γ-butyrolacton-4-yl refer to structures VII and VIII, respectively. The wavy lines are intended to denote each of the two epimers and mixtures thereof.

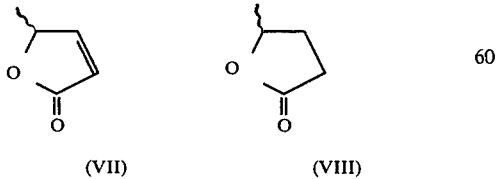

(VII)   (VIII)

When $R^1$ is an ester-forming residue readily hydrolyzable in vivo in a compound of formula I, it is a grouping which is notionally derived from an alcohol of the formula $R^1$-OH, such that the moiety $COOR^1$ in such a compound of formula I represents an ester grouping. Moreover, $R^1$ is of such a nature that the grouping $COOR^1$ is readily cleaved in vivo to liberate a free carboxy group (COOH). That is to say, $R^1$ is a group of the type that when a compound of formula I, wherein $R^1$ is an ester-forming residue readily hydrolyzed in vivo, is exposed to mammalian blood or tissue, the compound of formula I, wherein $R^1$ is hydrogen, is readily produced. The groups $R^1$ are well-known in the penicillin art. In most instances they improve the absorption characteristics of the penicillin compound. Additionally, $R^1$ should be of such a nature that it imparts pharmaceutically-acceptable properties to a compound of formula I, and it liberates pharmaceutically-acceptable fragments when cleaved in vivo.

As indicated above, the groups $R^1$ are well-known and are readily identified by those skilled in the penicillin at. See, for example, West German Offenlegungsschrift No. 2,517,316. Typical groups for $R^1$ are 3-phthalidyl, 4-crotonolactonyl, γ-butyrolacton-4-yl and groups of the formula

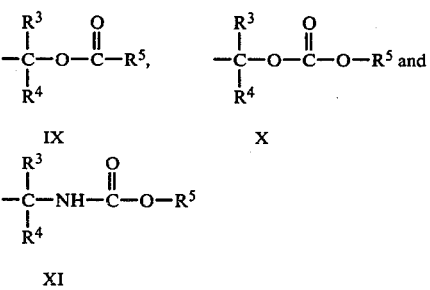

wherein $R^3$ and $R^4$ are each selected from the group consisting of hydrogen and alkyl having from 1 to 2 carbon atoms, and $R^5$ is alkyl having from 1 to 6 carbon atoms. However, preferred groups for $R^1$ are alkanoyloxymethyl having from 3 to 8 carbon atoms, 1-(alkanoyloxy)ethyl having from 4 to 9 carbon atoms, 1-methyl-1-alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)-aminomethyl having from 3 to 9 carbon atoms, 1-(N-[alkoxycarbonyl]amino)-ethyl having from 4 to 10 carbon atoms, 3-phthalidyl, 4-crotonolactonyl and γ-butyrolacton-4-yl.

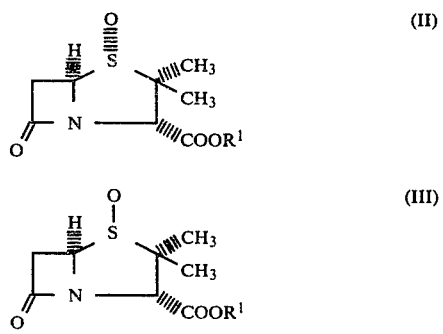

The compounds of formula I, wherein $R^1$ is as defined previously can be prepared by oxidation of either of the compounds of formula II or III, wherein $R^1$ is as defined previously. A wide variety of oxidants known in the art for the oxidation of sulfoxides to sulfones can be used for this process. However, particularly convenient reagents are metal permanganates, such the alkali metal permanganates and the alkaline earth metal permanganates, and organic peroxy acids, such as organic peroxycarboxylic acids. Convenient individual reagents are sodium permanganate, potassium permanganate, 3-chloroperbenzoic acid and peracetic acid.

When a compound of the Formula II or III, wherein $R^1$ is as defined previously, is oxidized to the corresponding compound of the formula I using a metal permanganate, the reaction is usually carried out by treating the compound of the formula II or III with from about 0.5 to about 5 molar equivalents of the permanganate, and preferably about 1 molar equivalent of the permanganate, in an appropriate solvent system. An appropriate solvent system is one that does not adversely interact with either the starting materials or the product, and water is commonly used. If desired, a co-solvent which is miscible with water but will not interact with the permanganate, such as tetrahydrofuran, can be added. The reaction is normally carried out at a temperature in the range from about $-20°$ to about $50°$ C., and preferably at about $0°$ C. At about $0°$ C. the reaction is normally substantially complete within a short period, e.g. within one hour. Although the reaction can be carried out under neutral, basic or acid conditions, it is preferable to operate under substantially neutral conditions in order to avoid decomposition of the β-lactam ring system of the compond of the formula I. Indeed, it is often advantageous to buffer the pH of the reaction medium in the vicinity of neutrality. The product is recovered by conventional techniques. Any excess permanganate is usually decomposed using sodium bisulfite, and then if the product is out of solution, it is recovered by filtration. It is separated from manganese dioxide by extracting it into an organic solvent and removing the solvent by evaporation. Alternatively, if the product is not out of solution at the end of the reaction, it is isolated by the usual procedure of solvent extraction.

When a compound of the formula II or III, wherein $R^1$ is as previously defined, is oxidized to the corresponding compound of the formula I, using an organic peroxy acid, e.g., a peroxycarboxylic acid, the reaction is usually carried out by treating the compound of the formula II or III with from about 1 to about 4 molar equivalents, and preferably about 1.2 equivalents of the oxidant in a reaction-inert organic solvent. Typical solvents are chlorinated hydrocarbons, such as dichloromethane, chloroform and 1,2-dichloroethane; and ethers, such as diethyl ether, tetrahydrofuran and 1,2-dimethoxyethane. The reaction is normally carried out at a temperature of from about $-20°$ to about $50°$ C., and preferably at about $25°$ C. At about $25°$ C. reaction times of about 2 to about 16 hours are commonly used. The product is normally isolated by removal of the solvent by evaporation in vacuo. The product can be purified by conventional methods, well-known in the art.

When oxidizing a compound of the formula II or III to a compound of the formula I using an organic peroxy acid, it is sometimes advantageous to add a catalyst such as a manganese salt, e.g. manganic acetylacetonate.

In like manner, compounds of the formula I, wherein $R^1$ is as previously defined, can be prepared by oxidation of a compound of the formula

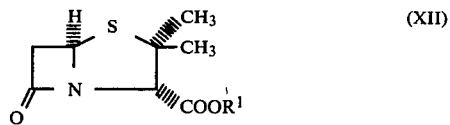

(XII)

wherein $R^1$ is as previously defined. This is carried out in exactly the same manner as described hereinbefore for oxidation of a compound of the formula II or III, except that twice as much oxidant is usually used.

Compounds of the formula I, wherein $R^1$ is an ester-forming residue readily hydrolyzable in vivo, can be prepared directly from the compound of formula I, wherein $R^1$ is hydrogen, by esterification. The specific method chosen will depend naturally upon the precise structure of the ester-forming residue, but an appropriate method will be readily selected by one skilled in the art. In the case wherein $R^1$ is selected from the group consisting of 3-phthalidyl, 4-crotonolactonyl, γ-butyrolacton-4-yl and groups of the formula IX, X and XI, wherein $R^3$, $R^4$ and $R^5$ are as defined previously, they can be prepared by alkylation of the compound of formula I, wherein $R^1$ is hydrogen, with a 3-phthalidyl halide, a 4-crotonolactonyl halide, a γ-butyrolacton-4-yl halide or a compound of the formula

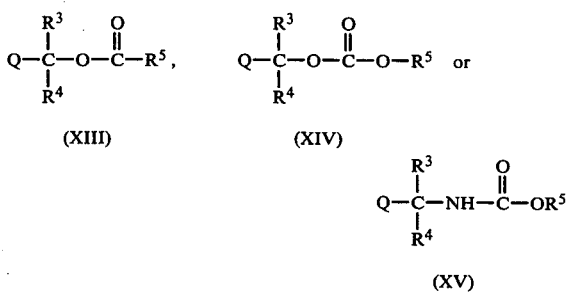

wherein Q is halo, and $R^3$, $R^4$ and $R^5$ are as previously defined. The terms "halide" and "halo" are intended to mean derivatives of chlorine, bromine and iodine. The reaction is conveniently carried out by dissolving a salt of the compound of formula I, wherein $R^1$ is hydrogen, in a suitable, polar, organic solvent, such as N,N-dimethylformamide, and then adding about one molar equivalent of the halide. When the reaction has proceeded essentially to completion, the product is isolated by standard techniques. It is often sufficient simply to dilute the reaction medium with an excess of water, and then extract the product into a water-immiscible organic solvent and then recover same by solvent evaporation. Salts of the starting material which are commonly used are alkali metal salts, such as sodium and potassium salt, and tertiary amine salts, such as triethylamine, N-ethylpiperidine, N,N-dimethylaniline and N-methylmorpholine salts. The reaction is run at a temperature in the range from about $0°$ to $100°$ C., and usually at about $25°$ C. The length of time needed to reach completion varies according to a variety of factors, such as the concentration of the reactants and the reactivity of the reagents. Thus, when considering the halo compound, the iodide reacts faster than the bromide, which in turn reacts faster than the chloride. In fact, it is sometimes advantageous, when utilizing a chloro compound, to add up to one molar equivalent of an alkali metal iodide. This has the effect of speeding up the reaction. With full regard for the foregoing factors, reaction times of from about 1 to about 24 hours are commonly used.

Penicillanic acid 1α-oxide, the compound of the formula II, wherein $R^1$ is hydrogen, can be prepared by debromination of 6,6-dibromopenicillanic acid 1α-oxide. The debromination can be carried out using a conventional hydrogenolysis technique. Thus, a solution of 6,6-dibromopenicillanic acid 1α-oxide is stirred or shaken under an atmosphere of hydrogen, or hydrogen mixed with an inert diluent such as nitrogen or argon, in the presence of a catalytic amount of palladium-on-calcium carbonate catalyst. Convenient solvents for this debromination are lower-alkanols, such as methanol; ethers, such as tetrahydrofuran and dioxan; low molecular weight esters, such as ethyl acetate and butyl acetate; water; and mixtures of these solvents. However, it is usual to choose conditions under which the dibromo compound is soluble. The hydrogenolysis is usually carried out at room temperature and at a pressure from about atmospheric pressure to about 50 p.s.i. The catalyst is usually present in an amount from about 10 percent by weight based on the dibromo compound, up to an amount equal in weight to the dibromo compound, although larger amounts can be used. The reaction commonly takes about one hour, after which the compound of the formula II, wherein $R^1$ is hydrogen, is recovered simply by filtration followed by removal of the solvent in vacuo.

6,6-Dibromopenicillanic acid 1α-oxide is prepared by oxidation of 6,6-dibromopenicillanic acid with 1 equivalent of 3-chloroperbenzoic acid in tetrahydrofuran at 0°–25° C. for ca. 1 hour, according to the procedure of Harrison et al., *Journal of the Chemical Society* (London) Perkin I, 1772 (1976). 6,6-Dibromopenicillanic acid is prepared by the method of Clayton, *Journal of the Chemical Society* (London), (C) 2123 (1969).

Penicillanic acid 1-β-oxide, the compound of the formula III, wherein $R^1$ is hydrogen, can be prepared by controlled oxidation of penicillanic acid. Thus, it can be prepared by treating penicillanic acid with one molar equivalent of 3-chloroperbenzoic acid in an inert solvent at about 0° C. for about one hour. Typical solvents which can be used include chlorinated hydrocarbons, such as chloroform and dichloromethane; ethers, such as diethyl ether and tetrahydrofuran; and low molecular weight esters such as ethyl acetate and butyl acetate. The product is recovered by conventional techniques.

Penicillanic acid is prepared as described in British Pat. No. 1,072,108.

Compounds of the formula II and III, wherein $R^1$ is an esterforming residue readily hydrolyzable in vivo, can be prepared directly from the compound of formula II or III, wherein $R^1$ is hydrogen, by esterification, using standard procedures. In the case wherein $R^1$ is selected from the group consisting of 3-phthalidyl, 4-crotonolactonyl, γ-butyrolacton-4-yl and groups of the formula, IX, X and XI, wherein $R^3$, $R^4$ and $R^5$ are as defined previously, they can be prepared by alkylation of the appropriate compound of the formula II or III, wherein $R^1$ is hydrogen, with 3-phthalidyl halide, 4-crotonolactonyl halide, a γ-butyrolacton-4-yl halide, or a compound of the formula XIII, XIV or XV. The reaction is carried out in exactly the same manner as described previously for esterification of penicillanic acid 1,1-dioxide with a 3-phthalidyl halide, a 4-crotonolactonyl halide, a γ-butyrolacton-4-yl halide, or a compound of the formula XIII, XIV or XV.

Alternatively, the compounds of the formula II, wherein $R^1$ is an ester-forming residue readily hydrolyzable in vivo, can be prepared by oxidation of the appropriate ester of 6,6-dibromopenicillanic acid, followed by debromination. The esters of 6,6-dibromopenicillanic acid are prepared from 6,6-dibromopenicillanic acid by standard methods. The oxidation is carried out, for example, by oxidation with one molar equivalent of 3-chloroperbenzoic acid, as described previously for the oxidation of 6,6-dibromopenicillanic acid to 6,6-dibromopenicillanic acid 1α-oxide; and the debromination is carried out as described previously for the debromination of 6,6-dibromopenicillanic acid 1α-oxide.

In like manner, the compounds of the formula III, wherein $R^1$ is an ester-forming residue readily hydrolyzable in vivo can be prepared by oxidation of the appropriate ester of penicillanic acid. The latter compounds are readily prepared by esterification of penicillanic acid using standard methods. The oxidation is carried out, for example, by oxidation with one molar equivalent of 3-chloroperbenzoic acid, as described previously for the oxidation of penicillanic acid to penicillanic acid 1β-oxide.

In an alternate method, the compounds of formula I, wherein $R^1$ is selected from the group consisting of hydrogen, and ester-forming residues readily hydrolyzable in vivo, can be prepared by a two-step procedure which comprises the steps of:

(a) contacting a compound selected from the group consisting of

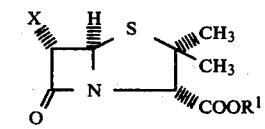 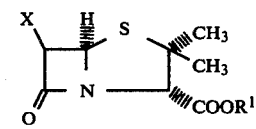

(XVI)    (XVII)

and base salts thereof with a reagent selected from the group consisting of alkali metal permanganates, alkaline earth metal permanganates and organic peroxycarboxylic acids, to give a compound selected from the group consisting of

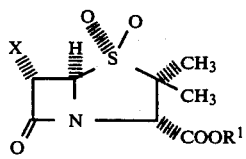 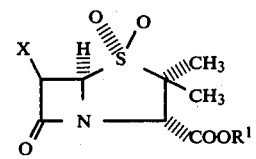

(XVIII)    (XIX)

and base salts thereof, wherein X is selected from the group consisting of chloro, bromo, and iodo; and (b) dehalogenating the compound of the formula XVIII or XIX or mixture thereof.

A preferred way of carrying out step (b) comprises contacting the product of step (a) with hydrogen, in an inert solvent, at a pressure in the range from about 1 to about 100 kg/cm², at a temperature in the range from about 0° to 60° C., and at a pH in the range from about 4 to about 9, and in the presence of a hydrogenolysis catalyst. The hydrogenolysis catalyst is usually present in an amount from about 0.01 to about 2.5 weight-percent, and preferably from about 0.1 to about 1.0 weight-percent, based on the halo-sulfone. The preferred value for X is bromo, and the preferred reagents for carrying out step (a) are potassium permanganate and 3-chloroperbenzoic acid.

In a further alternate method, the compounds of formula I, wherein $R^1$ is selected from the group consisting of hydrogen, and ester-forming residues readily hydrolyzable in vivo, can be prepared by a further two-step procedure which comprises the steps of (c) contacting a compound of the formula

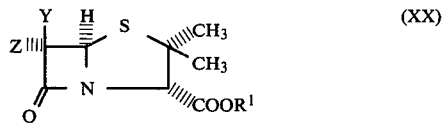

or a base salt thereof with a reagent selected from the group consisting of alkali metal permanganates, alkaline earth metal permanganates and organic peroxycarboxylic acids, to give a compound of the formula

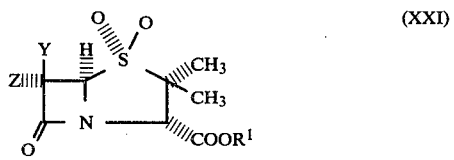

or a base salt thereof, wherein Y and Z are each selected from the group consisting of chloro, bromo and iodo; provided that Y and Z are not both chloro and Y and Z are not both iodo; and (d) dehalogenating the compound of formula XXI.

A preferred way of carrying out step (d) comprises contacting the product of step (c) with hydrogen, in an inert solvent, at a pressure in the range from about 1 to about 100 kg/cm², at a temperature in the range from about 0° to about 60° C., and at a pH in the range from about 4 to about 9, and in the presence of a hydrogenolysis catalyst. The hydrogenolysis catalyst is usually present in an amount from about 0.01 to about 2.5 weight-percent, and preferably from about 0.1 to about 1.0 weight-percent, based on the dihalo-sulfone.

The preferred value for Y and Z is bromo, and the preferred reagents for carrying out step (c) are potassium permanganate and 3-chloroperbenzoic acid.

In the case wherein Y and Z are both chloro, the compound of formula XX is difficult to obtain. In the case wherein Y and Z are both iodo, step (c) of the above process proceeds inconveniently slowly.

The compounds of formulas I, II and III, wherein $R^1$ is hydrogen, are acidic and will form salts with basic agents. These salts can be prepared by standard techniques, such as contacting the acidic and basic components, usually in a 1:1 molar ratio, in an aqueous, non-aqueous or partially aqueous medium, as appropriate. They are then recovered by filtration, by precipitation with a non-solvent followed by filtration, by evaporation of the solvent, or in the case of aqueous solutions, by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine and octylamine; secondary amines, such as diethylamine, morpholine, pyrrolidine and piperidine; tertiary amines, such as triethylamine, N-ethylpiperidine, N-methylmorpholine and 1,5-diazabicyclo[4.3.0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; bicarbonates, such as sodium bicarbonate and potassium bicarbonate; and alkali metal salts of long-chain fatty acids, such as sodium 2-ethylhexanoate.

Preferred salts of the compounds of the formulas I, II and III are sodium, potassium and triethylamine salts.

The compounds of formula I, wherein $R^1$ is hydrogen or an ester-forming residue readily hydrolyzable in vivo, are antibacterial agents of medium potency. The in vitro activity of the compound of the formula I, wherein $R^1$ is hydrogen, can be demonstrated by measuring its minimum inhibitory concentrations (MIC's) in mcg/ml against a variety of microorganisms. The procedure which is followed is the one recommended by the International Collaborative Study on Antibiotic Sensitivity Testing (Ericcson and Sherris, *Acta. Pathologica et Microbiologia* Scandinav, Supp. 217, Sections A and B: 64–68 [1971]), and employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg./ml. Single colonies are disregarded when reading plates after 18 hrs. at 37° C. The susceptibility (MIC) of the test organism is accepted as the lowest concentration of compound capable of producing complete inhibition of growth as judged by the naked eye. MIC values for penicillanic acid 1,1-dioxide against several microorganisms are shown in Table I.

TABLE I

In Vitro Antibacterial Activity of Penicillanic Acid 1,1-Dioxide

| Microorganism | MIC (mcg./ml.) |
|---|---|
| *Staphylococcus aureus* | 100 |
| *Streptococcus faecalis* | >200 |
| *Streptococcus pyogenes* | 100 |
| *Escherichia coli* | 50 |
| *Pseudomonas aeruginosa* | 200 |
| *Klebsiella pneumoniae* | 50 |
| *Proteus mirabilis* | 100 |
| *Proteus morgani* | 100 |
| *Salmonella typhimurium* | 50 |
| *Pasteurella multocida* | 50 |
| *Serratia marcescens* | 100 |
| *Enterobacter aerogenes* | 25 |
| *Enterobacter clocae* | 100 |
| *Citrobacter freundii* | 50 |
| *Providencia* | 100 |
| *Staphylococcus epidermis* | 200 |
| *Pseudomonas putida* | >200 |
| *Hemophilus influenzae* | >50 |
| *Neisseria gonorrhoeae* | 0.312 |

The compounds of the formula I, wherein $R^1$ is hydrogen or an ester-forming residue readily hydrolyzable in vivo, are active as antibacterial agents in vivo. In determining such activity, acute experimental infections are produced in mice by the intraperitoneal inoculation of the mice with a standardized culture of the test organism suspended in 5 percent hog gastric mucin. Infection severity is standardized so that the mice receive one to ten times the $LD_{100}$ dose of the organism ($LD_{100}$: the minimum inoculum of organism required to consistently kill 100 percent of the infected, non-treated control mice). The test compound is administered to the infected mice using a multiple dosage regimen. At the end of the test, the activity of a compound is assessed by counting the number of survivors among the treated animals and expressing the activity of a compound as the percentage of animals which survive.

The in vitro antibacterial activity of the compound of the formula I wherein $R^1$ is hydrogen makes it useful as an industrial antimicrobial, for example in water treatment, slime control, paint preservation and wood preservation, as well as for topical application as a disinfectant. In the case of use of this compound for topical application, it is often convenient to admix the active ingredient with a non-toxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

The in vivo activity of the compounds of formula I, wherein $R^1$ is hydrogen or an ester-forming-residue readily hydrolyzable in vivo, makes them suitable for the control of bacterial infections in mammals, including man, by both the oral and parenteral modes of administration. The compounds will find use in the control of infections caused by susceptible bacteria in human subjects, e.g. infections caused by strains of *Neisseria gonorrhoeae*.

When considering therapeutic area use of a compound of the formula I, or a salt thereof, in a mammal, particularly man, the compound can be administered alone, or it can be mixed with pharmaceutically acceptable carriers or diluents. They can be administered orally or parenterally, i.e. intramuscularly, subcutaneously or intraperitoneally. The carrier or diluent is chosen on the basis of the intended mode of administration. For example, when considering the oral mode of administration, an antibacterial penam compound of formula I can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. However, pharmaceutical compositions containing an antibacterial agent of the formula I will likely contain from about 20% to about 95% of active ingredient. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous and intravenous use, sterile solutions of the above ingredient are usually prepared, and the pH of the solutions are suitably adjusted and buffered. For intravenous use, the total concantration of solutes should be controlled to render the preparation isotonic.

The antibacterial agents of formula I are of use in human subjects against susceptible organisms. The prescribing physician will ultimately determine the appropriate dose for a given human subject, and this can be expected to vary according to the age, weight, and response of the individual patient, as well as the nature and the severity of the patient's symptoms. The compounds of formula I will normally be used orally at dosages in the range from about 10 to about 200 mg. per kilogram of body weight per day, and parenterally at dosages from about 10 to about 400 mg, per kilogram of body weight per day. These figures are illustrative only, however, and in some cases it may be necessary to use dosages outside these limits.

However, as indicated hereinbefore, the compounds of the formula I, wherein $R^1$ is hydrogen or an ester-forming residue readily hydrolyzable in vivo, are potent inhibitors of microbial beta-lactamases, and they increase the antibacterial effectiveness of 7-(D-2-[4-ethyl-piperazin-2,3-dione-1-carboxamidol-2-[4-hydroxy-phenyl]acetamido)-3-([1-methyl-5-tetrazolyl]thiomethyl)-3-desacetoxymethylcephalosporanic acid and the pharmaceutically-acceptable salts thereof. The latter named compound is the compound of the formula

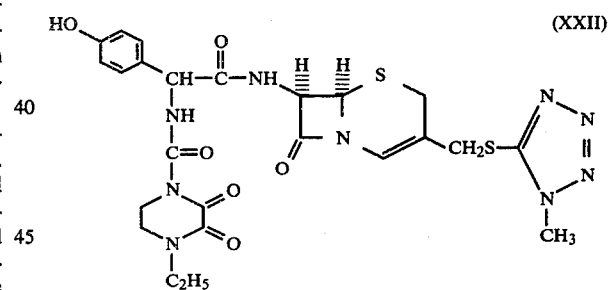

(XXII)

and methods for this preparation are described in U.S. Pat. No. 4,087,424 and Belgian Pat. No. 837,682. Whenever reference is made to be compound of formula XXII, said reference is also intended to embrace the pharmaceutically-acceptable salts thereof.

The manner in which the compounds of the formula I increase the effectiveness of the compound of formula XXII and the pharmaceutically-acceptable salts thereof can be appreciated by reference to experiments in which the MIC of the compound of the formula XXII alone, and the compound of the formula I wherein $R^1$ is hydrogen alone, are measured. These MIC's are then compared with the MIC values obtained with a combination of the compound of formula XXII and the compound of the formula I, wherein $R^1$ is hydrogen. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd edition, 1974, American Society of Microbiology.

The compounds of formula I are particularly useful for enhancing the antibacterial effectiveness of the compound of formula XXII against ampicillin-resistant strain of *Escherichia coli* and Bacteroides spp.

The compounds of the formula I, wherein $R^1$ is hydrogen or an ester-forming residue readily hydrolyzable in vivo, and salt thereof, enhance the antibacterial effectiveness of the compound of formula XXII in vivo. This is, they lower amount of the compound of formula XXII which is needed to protect mice against an otherwise lethal inoculum of certain beta-lactamase producing bacteria.

The ability of the compounds of the formula I, wherein $R^1$ is hydrogen or an ester-forming residue readily hydrolyzable in vivo, and salts thereof, to enhance the effectiveness of the compound of formula XXII against beta-lactamase-producing bacteria makes them valuable for co-administration with the compound of formula XXII in the treatment of bacterial infections in mammals, particularly man. In the treatment of a bacterial infection, said compound of the formula I or salt thereof can be comingled with the compound of formula XXII, and the two agents thereby administered simultaneously. Alternatively, said compound of the formula I or salt thereof can be administered as a separate agent during a course of treatment with the compound of formula XXII. In some instances it will be advantageous to pre-dose the subject with the compound of the formula I or salt thereof before initiating treatment with the compound of formula XXII.

When a compound of formula I or salt thereof is used as a separate agent during a course of treatment with the compound of formula XXII, the compound of formula I can be administered orally or parenterally, which includes intramuscular, subcutaneous and intraperitoneal use. For these purposes, the compound of formula I or salt thereof is administered preferably in formulation with standard pharmaceutical carriers of diluents. The methods of formulation discussed earlier for use of a compound of formula I as a single-entity antibacterial agent can be used.

When a compound of the formula I or salt thereof and the compound of formula XXII are to be co-mingled for co-administration to a mammal, it is also preferable to add a pharmaceutical carrier or diluent. Additionally, in this instance, it is preferable to prepare a formulation suitable for parenteral administration, since the compound of formula XXII is more effective when administered parenterally. Parenteral use includes intramuscular subcutaneous and intraperitoneal use. For these purposes, the compound of formula I, or salt thereof, and the compound of formula XXII are co-formulated using the methods discussed earlier for preparation of a pharmaceutical composition of a compound of formula I suitable for parenteral use. A pharmaceutical composition comprising a pharmaceutically-acceptable carrier, the compound of the formula XXII, and a compound of formula I or salt thereof will normally contain from about 5 to about 80 percent of the pharmaceutically-acceptable carrier by weight.

Although the prescribing physician will ultimately decide the dosages of the compound of formula XXII and a compound of formula I salt thereof, the ratio of the daily dosages of the two compounds will normally be in the range from about 1:6 to about 6:1 by weight, and preferably 1:2 to 2:1. Additionally, the daily parenteral dosage of each component will normally be in the range from about 5 to about 100 mg. per kilogram of body weight, and preferably from about 10 to about 50 mg. per kilogram of body weight. The daily oral dosage of a compound of formula I or salt thereof will normally be about 5 to about 100 mg. per kilogram of body weight and preferably from about 10 to about 50 mg. per kilogram of body weight. These figures are illustrative only, however, and in some cases it may be necessary to use dosages outside these limits.

The following examples are provided solely for the purpose of further illustration. Infrared (IR) spectra were measured as potassium bromide discs (KBr discs) or an Nujol mulls, and diagnostic absorption bands are reported in wave numbers ($cm^{-1}$). Nuclear magnetic resonance spectra (NMR) were measured at 60 MHz for solutions in deuterochloroform ($CDCl_3$), perdeutero dimethyl sulfoxide (DMSO-$d_6$) or deuterium oxide ($D_2O$), and peak positions are expressed in parts per million (ppm) downfield from tetramethylsilane or sodium 2,2-dimethyl-2-silapentane-5-sulfonate. The following abbreviations for peak shapes are used: s, singlet; d, doublet; t, triplet; q, quartet; m, multiplet.

EXAMPLE 1

Penicillanic Acid 1,1-Dioxide

To a solution of 6.51 g. (41 mmole) of potassium permanganate in 130 ml. of water and 4.95 ml. of glacial acetic acid, cooled to ca. 5° C., was added a cold (ca. 5° C.) solution of 4.58 g. (21 mmole) of the sodium salt of penicillanic acid in 50 ml. of water. The mixture was stirred at ca. 5° C. for 20 minutes and then the cooling bath was removed. Solid sodium bisulfite was added until the color of the potassium permanganate had been discharged, and then the mixture was filtered. To the aqueous filtrate was added half its volume of saturated sodium chloride solution, and then the pH was adjusted to 1.7. The acidic solution was extracted with ethyl acetate. The extracts were dried, and the evaporated in vacuo, to give 3.47 g. of the title product. The aqueous mother liquor was saturated with sodium chloride, and further extracted with ethyl acetate. The ethyl acetate solution was dried and evaporated in vacuo, to give a further 0.28 g. of product. The total yield was therefore 3.75 g. (78% yield). The NMR spectrum (DMSO-$d_6$) of the product showed absorptions at 1.40 (s, 3H), 1.50 (s, 3H), 3.13 (d of d's, 1H, $J_1=16$ Hz, $J_2=2$ Hz), 3.63 (d of d's, 1H, $J_1=16$ Hz, $J_2=4$ Hz), 4.22 (s, 1H) and 5.03 (d of d's, 1H, $J_1=4$ Hz, $J_2=2$ Hz) ppm.

EXAMPLE 2

Benzyl Penicillanate 1,1-Dioxide

To a stirred solution of 6.85 g. (24 mmole) of benzyl penicillanate in 75 ml. of ethanol-free chloroform, under nitrogen, in an ice-bath, was added in two portions, several minutes apart, 4.78 g. of 85% pure 3-chloroperbenzoic acid. Stirring was continued for 30 minutes in the ice-bath, and then for 45 minutes without external cooling. The reaction mixture was washed with aqueous alkali (pH 8.5), followed by saturated sodium chloride, and then it was dried and evaporated in vacuo to give 7.05 g. of residue. Examination of this residue showed it to be a 5.5:1 mixture of benzyl penicillanate 1-oxide and benzyl penicillanate 1,1-dioxide.

To a stirred solution of 4.85 g. of the above 5.5:1 sulfoxidesulfone mixture in 50 ml. of ethanol-free chloroform, under nitrogen, was added 3.2 g. of 85% pure 3-chloroperbenzoic acid at room temperature. The reaction mixture was stirred for 2.5 hours, and then it was diluted with ethyl acetate. The resultant mixture was added to water at pH 8.0, and then the layers were separated. The organic phase was washed with water at pH 8.0, followed by saturated sodium chloride, and then it was dried using sodium sulfate. Evaporation of the solvent in vacuo afforded 3.59 g. of the title compound. The NMR spectrum of the product (in CDCl$_3$) showed absorptions at 1.28 (s, 3H), 1.58 (s, 3H), 3.42 (m, 2H), 4.37 (s, 1H), 4.55 (m, 1H), 5.18 (q, 2H, J=12 Hz) and 7.35 (s, 5H) ppm.

EXAMPLE 3

Penicillanic Acid 1,1-Dioxide

To a stirred solution of 8.27 g. of benzyl penicillanate 1,1-dioxide in a mixture of 40 ml. of methanol and 10 ml. of ethyl acetate was slowly added 10 ml. of water, followed by 12 g. of 5% palladium-on-calcium carbonate. The mixture was shaken under an atmosphere of hydrogen, at 52 psi, for 40 minutes, and then it was filtered through supercel (a diatomaceous earth). The filter cake was washed with methanol, and with aqueous methanol, and the washings were added to the filtrate. The combined solution was evaporated in vacuo to remove the majority of the organic solvents and then the residue was partitioned between ethyl acetate and water at a pH of 2.8. The ethyl acetate layer was removed and the aqueous phase was further extracted with ethyl acetate. The combined ethyl acetate solutions were washed with saturated sodium chloride solution, dried using sodium sulfate and then evaporated in vacuo. The residue was slurried in a 1:2 mixture of ethyl acetate-ether, to give 2.37 g. of the title product having a melting point of 148°–51° C. The ethyl acetate-ether mixture was evaporated giving a further 2.17 g. of product.

EXAMPLE 4

Pivaloyloxymethyl Penicillanate 1,1-Dioxide

To 0.615 g. (2.41 mmole) of penicillanic acid 1,1-dioxide in 2 ml. of N,N-dimethylformamide was added 0.215 g. (2.50 mmole) of diisopropylethylamine followed by 0.365 ml. of chloromethyl pivalate. The reaction mixture was stirred at room temperature for 24 hours, and then it was diluted with ethyl acetate and water. The ethyl acetate layer was separated and washed three times with water and once with saturated sodium chloride solution. The ethyl acetate solution was then dried using anhydrous sodium sulfate, and evaporated in vacuo to give 0.700 g. of the title product as a solid, mp 103°–4° C. The NMR spectrum of the product (in CDCl$_3$) showed absorptions at 1.27 (s, 9H), 1.47 (s, 3H), 1.62 (s, 3H), 3.52 (m, 2H), 4.47 (s, 1H), 4.70 (m, 1H), 5.73 (d, 1H, J=6.0 Hz) and 5.98 (d, 1H, J=6.0 Hz).

EXAMPLE 5

The procedure of Example 4 is repeated, except that the pivaloyoxymethyl chloride used therein is replaced by an equimolar amount of acetoxymethyl chloride, propionyloxymethyl chloride and hexanoyloxymethyl chloride, respectively, to give:
acetoxymethyl penicillanate 1,1-dioxide,
propionyloxymethyl penicillanate 1,1-dioxide and
hexanoyloxymethyl penicillanate 1,1-dioxide, respectively.

EXAMPLE 6

3-Phthalidyl Penicillanate 1,1-Dioxide

To 0.783 g. (3.36 mmole) of penicillanic acid 1,1-dioxide in 5 ml. of N,N-dimethylformamide was added 0.47 ml. of triethylamine followed by 0.715 g. of 3-bromophthalide. The reaction mixture was stirred for 2 hours at room temperature and then it was diluted with ethyl acetate and water. The pH of the aqueous phase was raised to 7.0 and the layers were separated. The ethyl acetate layer was washed successively with water and saturated sodium chloride solution, and then it was dried using sodium sulfate. The ethyl acetate solution was evaporated in vacuo leaving the title product as a white foam. The NMR spectrum of the product (in CDCl$_3$) showed absorptions at 1.47 (s, 6H), 3.43 (m, 1H), 4.45 (s, 1H), 4.62 (m, 1H), 7.40 and 7.47 (2s's, 1H) and 7.73 (m, 4H) ppm When the above procedure is repeated, except that the 3-bromophthalide is replaced by 4-bromo-crotonolactone and 4-bromo-γ-butyrolactone, respectively, this affords:
4-crotonolactonyl penicillanate 1,1-dioxide and
γ-butyrolacton-4-yl penicillanate, 1,1-dioxide, respectively.

EXAMPLE 7

1-(Ethoxycarbonyloxy)ethyl Penicillanate 1,1-Dioxide

A mixture of 0.654 g. of penicillanic acid 1,1-dioxide, 0.42 ml. of triethylamine, 0.412 g. of 1-chloroethyl ethyl carbonate, 0.300 g. of sodium bromide and 3 ml. of N,N-dimethylformamide was stirred at room temperature for 6 days. It was then worked up by diluting it with ethyl acetate and water, and then the pH was adjusted to 8.5. The ethyl acetate layer was separated, washed three times with water, washed once with saturated sodium chloride, and then it was dried using anhydrous sodium sulfate. The ethyl acetate was removed by evaporation in vacuo leaving 0.390 g. of the title product as an oil.

The above product was combined with an approximately equal amount of similar material from a similar experiment. The combined product was dissolved in chloroform and 1 ml. of pyridine was added. The mixture was stirred at room temperature overnight and then the chloroform was removed by evaporation in vacuo. The residue was partitioned between ethyl acetate and water at pH 8. The separated and dried ethyl acetate was then evaporated in vacuo to give 150 mg. of the title product (yield ca 7%). The IR spectrum (film) of the product showed absorptions at 1805 and 1763 cm$^{-1}$. The NMR spectrum (CDCl$_3$) showed absorptions at 1.43 (m, 12H), 3.47 (m, 2H), 3.9 (q, 2H, J=7.5 Hz), 4.37/m, 1H), 4.63 (m, 1H) and 6.77 (m, 1H) ppm.

EXAMPLE 8

The procedure of Example 7 is repeated, except that the 1-chloroethyl ethyl carbonate is replaced by an equimolar amount of the appropriate 1-chloroalkyl alkyl carbonate, 1-(alkanoyloxy)ethyl chloride or 1-methyl-1-(alkanoyloxy)ethyl chloride, to produce the following compounds:
methoxycarbonyloxymethyl penicillanate 1,1-dioxide,
ethoxycarbonyloxymethyl penicillanate 1,1-dioxide,
isobutoxycarbonyloxymethyl penicillanate 1,1-dioxide, 1-(methoxycarbonyloxy)ethyl penicillanate 1,1-dioxide,
1-(butoxycarbonyloxy)ethyl penicillanate 1,1-dioxide,
1-(acetoxy)ethyl penicillanate 1,1-dioxide,
1-(butyryloxy)ethyl penicillanate 1,1-dioxide,
1-(pivaloyloxy)ethyl penicillanate 1,1-dioxide,
1-(hexanoyloxy)ethyl penicillanate 1,1-dioxide,
1-methyl-1-(acetoxy)ethyl penicillanate 1,1-dioxide and
1-methyl-1-(isobutyryloxy)ethyl penicillanate 1,1-dioxide, respectively.

EXAMPLE 9

The procedure of Example 4 is repeated, except that the chloromethyl pivalate is replaced by an equimolar amount of benzyl bromide and 4-nitrobenzyl bromide, respectively, to produce benzyl penicillanate 1,1-dioxide and 4-nitrobenzyl penicillanate 1,1-dioxide, respectively.

EXAMPLE 10

Penicillanic Acid 1α-Oxide

To 1.4 g. of prehydrogenated 5% palladium-on-calcium carbonate in 50 ml. of water was added a solution of 1.39 g. of benzyl 6,6-dibromopenicillanate 1α-oxide in 50 ml. of tetrahydrofuran. The mixture was shaken under an atmosphere of hydrogen at ca. 45 p.s.i. and 25° C. for 1 hour, and then it was filtered. The filtrate was evaporated in vacuo to remove the bulk of the tetrahydrofuran, and then the aqueous phase was extracted with ether. The ether extracts were evaporated in vacuo to give 0.5 g. of material which appeared to be largely benzyl penicillanate 1α-oxide.

The above benzyl penicillanate 1α-oxide was combined with a further 2.0 g. of benzyl 6,6-dibromopenicillanate 1α-oxide and dissolved in 50 ml. of tetrahydrofuran. The solution was added to 4.0 g. of 5% palladium-on-calcium carbonate, in 50 ml. of water, and the resulting mixture was shaken under an atmosphere of hydrogen, at ca. 45 p.s.i. and 25° C. overnight. The mixture was filtered, and the filtrate was extracted with ether. The extracts were evaporated in vacuo, and the residue was purified by chromatography on silica gel, eluting with chloroform. This afforded 0.50 g. of material.

The latter material was hydrogenated at ca. 45 p.s.i. at 25° C. in water-methanol (1:1) with 0.50 g. of 5% palladium-on-calcium carbonate for 2 hours. At this point, an additional 0.50 g. of 5% palladium-on-calcium carbonate was added and the hydrogenation was continued at 45 p.s.i. and 25° C. overnight. The reaction mixture was filtered, extracted with ether and the extracts were discarded. The residual aqueous phase was adjusted to pH 1.5 and then extracted with ethyl acetate. The ethyl acetate extracts were dried (Na$_2$SO$_4$) and then evaporated in vacuo to give 0.14 g. of penicillanic acid 1α-oxide. The NMR spectrum (CDCl$_3$/DMSO-d$_6$) showed absorptions at 1.4 (s, 3H), 1.64 (s, 3H), 3.60 (m, 2H), 4.3 (s, 1H) and 4.54 (m, 1H)ppm. The IR spectrum of the product (KBr disc) showed absorptions at 1795 and 1745 cm$^{-1}$.

EXAMPLE 11

Penicillanic Acid 1α-Oxide

To 1.0 g. of prehydrogenated 5% palladium-on-calcium carbonate in 30 ml. of water is added a solution of 1.0 g. of 6,6-dibromopenicillanic acid 1α-oxide. The mixture is shaken under an atmosphere of hydrogen, at ca. 45 p.s.i. and 25° C., for 1 hour. The reaction mixture is then filtered and the filtrate is concentrated in vacuo to remove the methanol. The residual aqueous phase is diluted with an equal volume of water, adjusted to pH 7, and washed with ether. The aqueous phase is then acidified to pH 2 with dilute hydrochloric acid and extracted with ethyl acetate. The ethyl acetate extracts are dried (Na$_2$SO$_4$) and evaporated in vacuo to give penicillanic acid 1α-oxide.

EXAMPLE 12

Penicillanic Acid 1β-Oxide

To a stirred solution of 2.65 g. (12.7 mmole) of penicillanic acid in chloroform at 0° C. was added 2.58 g. of 85% pure 3-chloroperbenzoic acid. After 1 hour, the reaction mixture was filtered and the filtrate was evaporated in vacuo. The residue was dissolved in a small amount of chloroform. The solution was concentrated slowly until a precipitate began to appear. At this point the evaporation was stopped and the mixture was diluted with ether. The precipitate was removed by filtration, washed with ether and dried, to give 0.615 g. of penicillanic acid 1β-oxide, m.p. 140°-3° C. The IR spectrum of the product (CHCl$_3$ solution) showed absorptions at 1775 and 1720 cm$^{-1}$. The NMR spectrum (CDCl$_3$/DMSO-d$_6$) showed absorptions at 1.35 (s, 3H), 1.76 (s, 3H), 3.36 (m, 2H), 4.50 (s, 1H) and 5.05 (m, 1H) ppm. From the NMR spectrum, the product appeared to be ca. 90% pure.

Examination of the chloroform-ether mother liquor revealed that it contained further penicillanic acid 1β-oxide, and also some penicillanic acid 1α-oxide.

EXAMPLE 13

Esterification of penicillanic acid 1α-oxide or penicillanic acid 1β-oxide, as appropriate, with the requisite alkanoyloxy chloride, according to Example 5, provides the following compounds:
acetoxymethyl penicillanate 1α-oxide,
propionyloxymethyl penicillanate 1α-oxide,
pivaloyoxymethyl penicillanate 1α-oxide,
acetoxymethyl penicillanate 1β-oxide,
propionyloxymethyl penicillanate 1β-oxide and
pivaloyloxymethyl penicillanate 1β-oxide, respectively.

EXAMPLE 14

Reaction of penicillanic acid 1α-oxide or penicillanic acid 1β-oxide with 3-bromophthalide, 4-bromocrotonolactone or 4-bromo-γ-butyrolactone, as appropriate, affords the following compounds:
3-phthalidyl penicillanate 1α-oxide
4-crotonolactonyl penicillanate 1α-oxide,
3-phthalidyl penicillanate 1β-oxide,
4-crotonolactonyl penicillanate 1β-oxide and
γ-butyrolacton-4-yl penicillanate 1β-oxide, respectively.

EXAMPLE 15

Reaction of penicillanic acid 1a-oxide or penicillanic acid 1b-oxide, as appropriate, with the requisite 1-chloroalkyl alkyl carbonate, 1-(alkanoyloxy)ethyl chloride, N-(alkoxycarbonyl)aminomethyl chloride or 1-(N-[alkoxycarbonyl]amino)ethyl chloride, according to the procedure of Example 7, provides the following compounds:
1-(ethoxycarbonyloxy)ethyl penicillanate 1α-oxide,
methoxycarbonyloxymethyl penicillanate 1α-oxide,
ethoxycarbonyloxymethyl penicillanate 1α-oxide,
isobutoxycarbonyloxymethyl penicillanate 1α-oxide, 1-(methoxycarbonyloxy)ethyl penicillanate 1α-oxide,
1-(butoxycarbonyloxy)ethyl penicillanate 1α-oxide,
1-(acetoxy)ethyl penicillanate 1α-oxide,
1-(butyryloxy)ethyl penicillanate 1α-oxide,
1-(pivaloyloxy)ethyl penicillanate 1α-oxide,
1-(ethoxycarbonyloxy)ethyl penicillanate 1β-oxide,
methoxycarbonyloxymethyl penicillanate 1β-oxide,
ethoxycarbonyloxymethyl penicillanate 1β-oxide,
isobutoxycarbonyloxymethyl penicillanate 1β-oxide,
1-(methoxycarbonyloxy)ethyl penicillanate 1β-oxide,
1-(butoxycarbonyloxy)ethyl penicillanate 1β-oxide,
1-(acetoxy)ethyl penicillanate 1β-oxide,
1-(butyryloxy)ethyl penicillanate 1β-oxide,
1-(pivaloyloxy)ethyl penicillanate 1β-oxide,
N-(methoxycarbonyl)aminomethyl penicillanate 1α-oxide,
N-(ethyloxycarbonyl)aminomethyl penicillanate 1α-oxide,
N-(hexyloxycarbonyl)aminomethyl penicillanate 1α-oxide,
1-(N-[methyloxycarbonyl]amino)ethyl penicillanate 1α-oxide,
1-(N-[isopropoxycarbonyl]amino)ethyl penicillanate 1α-oxide,
1-(N-[hexyloxycarbonyl]amino)ethyl penicillanate 1α-oxide,
N-(methoxycarbonyl)aminomethyl penicillanate 1β-oxide,
N-(ethoxycarbonyl)aminomethyl penicillanate 1β-oxide,
N-(hexyloxycarbonyl)aminomethyl penicillanate 1β-oxide,
1-(n-[methoxycarbonyl]amino)ethyl penicillanate 1β-oxide,
1-(N-[t-butoxycarbonyl]amino)ethyl penicillanate 1β-oxide and
1-(N-[hexyloxycarbonyl]amino)ethyl penicillanate 1β-oxide, respectively.

EXAMPLE 16

Reaction of penicillanic acid 1α-oxide and penicillanic acid 1β-oxide with benzyl bromide, according to the procedure of Example 4, produces benzyl penicillanate 1α-oxide and benzyl penicillanate 1β-oxide, respectively.

In like manner, reaction of penicillanic acid 1α-oxide and penicillanic acid 1β-oxide with 4-nitrobenzyl bromide, according to the procedure of Example 4, produces 4-nitrobenzyl penicillanate 1α-oxide and 4-nitrobenzyl penicillanate 1β-oxide, respectively.

EXAMPLE 17

Penicillanic Acid 1,1-Dioxide

To 2.17 g. (10 mmole) of penicillanic acid 1α-oxide in 30 ml. of ethanol-free chloroform at ca. 0° C. is added 1.73 g. (10 mmole) of 3-chloroperbenzoic acid. The mixture is stirred for 1 hour at ca. 0° C. and then for an additional 24 hours at 25° C. The filtered reaction mixture is evaporated in vacuo to give penicillanic acid 1,1-dioxide.

EXAMPLE 18

The procedure of Example 17 is repeated, except that the penicillanic acid 1α-oxide used therein is replaced by:
penicillanic acid 1β-oxide,
acetoxymethyl penicillanate 1α-oxide,
propionyloxymethyl penicillanate 1α-oxide,
pivaloyloxymethyl penicillanate 1α-oxide,
acetoxymethyl penicillanate 1β-oxide,
propionyloxymethyl penicillanate 1β-oxide,
pivaloyloxymethyl penicillanate 1β-oxide,
3-phthalidyl penicillanate 1α-oxide,
3-phthalidyl penicillanate 1β-oxide,
1-(ethoxycarbonyloxy)ethyl penicillanate 1α-oxide,
methoxycarbonyloxymethyl penicillanate 1α-oxide,
ethoxycarbonyloxymethyl penicillanate 1α-oxide,
isobutoxycarbonyloxymethyl penicillanate 1α-oxide,
1-(methoxycarbonyloxy)ethyl penicillanate 1α-oxide,
1-(butoxycarbonyloxy)ethyl penicillanate 1α-oxide,
1-(acetoxy)ethyl penicillanate 1α-oxide,
1-(butyryloxy)ethyl penicillanate 1α-oxide,
1-(pivaloyloxy)ethyl penicillanate 1α-oxide,
1-(ethoxycarbonyloxy)ethyl penicillanate 1β-oxide,
methoxycarbonyloxymethyl penicillanate 1β-oxide,
ethoxycarbonyloxymethyl penicillanate 1β-oxide,
isobutoxycarbonyloxymethyl penicillanate 1β-oxide,
1-(methoxycarbonyloxy)ethyl penicillanate 1β-oxide,
1-(butoxycarbonyloxy)ethyl penicillanate 1β-oxide,
1-(acetoxy)ethyl penicillanate 1β-oxide,
1-(butyryloxy)ethyl penicillanate 1β-oxide and
1-(pivaloyloxy)ethyl penicillanate 1β-oxide, respectively.

This affords:
penicillanic acid 1,1-dioxide,
acetoxymethyl penicillanate 1,1-dioxide,
propionyloxymethyl penicillanate 1,1-dioxide,
pivaloyoxymethyl penicillanate 1,1-dioxide,
acetoxymethyl penicillanate 1,1-dioxide,
propionyloxymethyl penicillanate 1,1-dioxide,
pivaloyloxymethyl penicillanate 1,1-dioxide,
3-phthalidyl penicillanate 1,1-dioxide,
3-phthalidyl penicillanate 1,1-dioxide,
1-(ethoxycarbonyloxy)ethyl penicillanate 1,1-dioxide,
methoxycarbonyloxymethyl penicillanate 1,1-dioxide,
ethoxycarbonyloxymethyl penicillanate 1,1-dioxide,
isobutoxycarbonyloxymethyl penicillanate 1,1-dioxide,
1-(methoxycarbonyloxy)ethyl penicillanate 1,1-dioxide,
1-(butoxycarbonyloxy)ethyl penicillanate 1,1-dioxide,
1-(acetoxy)ethyl penicillanate 1,1-dioxide,
1-(butyryloxy)ethyl penicillanate 1,1-dioxide,
1-(pivaloyloxy)ethyl penicillanate 1,1-dioxide,
1-(ethoxycarbonyloxy)ethyl penicillanate 1,1-dioxide,
methoxycarbonyloxymethyl penicillanate 1,1-dioxide,
ethoxycarbonyloxymethyl penicillanate 1,1-dioxide,
isobutoxycarbonyloxymethyl penicillanate 1,1-dioxide,
1-(methoxycarbonyloxy)ethyl penicillanate 1,1-dioxide,
1-(butoxycarbonyloxy)ethyl penicillanate 1,1-dioxide,
1-(acetoxy)ethyl penicillanate 1,1-dioxide,
1-(butyryloxy)ethyl penicillanate 1,1-dioxide and
1-(pivaloyloxy)ethyl penicillanate 1,1-dioxide, respectively.

EXAMPLE 19

Oxidation of benzyl penicillanate 1α-oxide and benzyl penicillanate 1β-oxide with 3-chloroperbenzoic acid, according to the procedure of Example 17, produces, in each case, benzyl penicillanate 1,1-dioxide.

In like manner, oxidation of 4-nitrobenzyl penicillanate 1α-oxide and 4-nitrobenzyl penicillanate 1β-oxide with 3-chloroperbenzoic acid, according to the procedure of Example 17, produces 4-nitrobenzyl penicillanate 1,1-dioxide.

EXAMPLE 20

Penicillanic Acid 1,1-Dioxide

Hydrogenolysis of 4-nitrobenzyl penicillanate 1,1-dioxide, according to the procedure of Example 3, affords penicillanic acid 1,1-dioxide.

EXAMPLE 21

Sodium Penicillanate 1,1-Dioxide

To a stirred solution of 32.75 g. (0.14 mole) of penicillanic acid 1,1-dioxide in 450 ml. of ethyl acetate was added a solution of 25.7 g. of sodium 2-ethylhexanoate (0.155 mole) in 200 ml. of ethyl acetate. The resulting solution was stirred for 1 hour and then an additional 10% excess of sodium 2-ethylhexanoate in a small volume of ethyl acetate was added. Product immediately began to precipitate. Stirring was continued for 30 minutes and then the precipitate was removed by filtration. It was washed sequentially with ethyl acetate, with 1:1 ethyl acetate-ether and with ether. The solid was then dried over phosphorus pentoxide, at ca. 0.1 mm of Hg for 16 hours at 25° C., giving 36.8 g. of the title sodium salt, contaminated with a small amount of ethyl acetate. The ethyl acetate content was reduced by heating to 100° C. for 3 hours under vacuum. The IR spectrum of this final product (KBr disc) showed absorptions at 1786 and 1608 cm$^{-1}$. The NMR spectrum (D$_2$O) showed absorptions at 1.48 (s, 3H), 1.62 (s, 3H), 3.35 (d of d's, 1H, $J_1=16$ Hz, $J_2=2$ Hz), 3.70 (d of d's, 1H, $J_1=16$ Hz, $J_2=4$ Hz), 4.25 (s, 1H) and 5.03 (d of d's, 1H, $J_1=4$ Hz, $J_2=2$ Hz) ppm.

The title sodium salt can also be prepared using acetone in place of ethyl acetate.

EXAMPLE 22

Penicillanic Acid 1,1-Dioxide

To a mixture of 7,600 ml. of water and 289 ml. of glacial acetic acid was added, portionwise, 379.5 g. of potassium permanganate. This mixture was stirred for 15 minutes, and then it was cooled to 0° C. To it was then added, with stirring, a mixture which had been prepared from 270 g. of penicillanic acid, 260 ml. of 4 N sodium hydroxide and 2,400 ml. of water (pH 7.2), and which had then been cooled to 8° C. The temperature rose to 15° C. during this latter addition. The temperature of the resulting mixture was reduced to 5° C. and the stirring was continued for 30 minutes. To the reaction mixture was then added 142.1 g. of sodium bisulfite, in portions, during 10 minutes. The mixture was stirred for 10 minutes at 10° C., and then 100 g. of supercel (a diatomaceous earth) was added. After a further 5 minutes of stirring, the mixture was filtered. To the filtrate was added 4.0 liters of ethyl acetate, and then the pH of the aqueous phase was lowered to 1.55 using 6 N hydrochloric acid. The ethyl acetate layer was removed and combined with several further ethyl acetate extracts. The combined organic layer was washed with water, dried (MgSO$_4$) and evaporated almost to dryness in vacuo. The slurry thus obtained was stirred with 700 ml. of ether at 10° C., for 20 minutes, and then the solid was collected by filtration. This afforded 82.6 g. (26% yield) of the title compound having a melting point of 154°–155.5° C. (dec.).

EXAMPLE 23

Pivaloyloxymethyl Penicillanate 1,1-Dioxide

To a solution of 1.25 g. pivaloyoxymethyl penicillanate in 40 ml. of chloroform, cooled to ca. −15° C., was added 0.8 g. of 3-chloroperbenzoic acid. The mixture was stirred at ca. −15° C. for 20 minutes and then it was allowed to warm to room temperature. Analysis of the resulting solution by NMR indicated that it contained both the 1α- and 1β-oxide.

The chloroform solution was concentrated to about 20 ml. and a further 0.8 g. of 3-chloroperbenzoic acid was added. This mixture was stirred overnight at room temperature, and then all the solvent was removed by evaporation in vacuo. The residue was redissolved in ca 4 ml. of dichloromethane and 0.4 g. of 3-chloroperbenzoic acid was added. The mixture was stirred for 3 hours and then the solvent was removed by evaporation in vacuo. The residue was partitioned between ethyl acetate and water at pH 6.0, and sodium bisulfite was added until a test for the presence of peroxides was negative. The pH of the aqueous phase was raised to 8.0 and the layers were separated. The organic layer was washed with brine, dried using anhydrous sodium sulfate and evaporated in vacuo. The residue was dissolved in ether and reprecipitated by the addition of hexane. The resulting solid was recrystallized from ether to give 0.357 g. of the title compound.

The NMR spectrum of the product (CDCl$_3$) showed absorptions at 1.23 (s, 9H), 1.50 (s, 3H), 1.67 (s, 3H), 3.28 (m, 2H), 4.45 (s, 1H), 5.25 (m, 1H) and 5.78 (m, 2H) ppm.

EXAMPLE 24

3-Phthalidyl Penicillanate 1,1-Dioxide

To a solution of 713 mg. of 3-phthalidyl penicillanate in 3 ml. of chloroform was added 0.430 g. of 3-chloroperbenzoic acid at ca. 10° C. The mixture was stirred for 30 minutes and then a further 0.513 g. of 3-chloroperbenzoic acid was added. The mixture was stirred for 4 hours at room temperature, and then the solvent was removed by evaporation in vacuo. The residue was partitioned between ethyl acetate and water at pH 6.0, and sodium bisulfite was added to decompose any remaining peracid. The pH of the aqueous phase was raised to 8.8. The layers were separated and the organic phase was evaporated in vacuo. This afforded the title compound as a foam. The NMR spectrum (CDCl$_3$) showed absorptions at 1.62 (m, 6H), 3.3 (m, 2H), 4.52 (p, 1H), 5.23 (m, 1H) and 7.63 (m, 5H) ppm.

EXAMPLE 25

2,2,2-Trichloroethyl Penicillanate 1,1-Dioxide

To 100 mg. of 2,2,2-trichloroethyl penicillanate in a small volume of chloroform was added 50 mg. of 3-chloroperbenzoic acid and the mixture was stirred for 30 minutes. Examination of the reaction product at this point revealed that it was mostly sulfoxide (The NMR spectrum (CDCl$_3$) showed absorptions at 1.6 (s, 3H), 1.77 (s, 3H), 3.38 (m, 2H), 4.65 (s, 1H), 4.85 (m, 2H) and 5.37 (m, 1H) ppm.) A further 100 mg. of 3-chloroperbenzoic acid was added and the mixture was stirred overnight. The solvent was then removed by evaporation in vacuo, and the residue was partitioned between ethyl acetate and water at pH 6.0. Sufficient sodium bisulfite was added to decompose the excess peracid and then the pH was raised to 8.5. The organic phase was separated, washed with brine and dried. Evaporation in vacuo afforded 65 mg. of the title product. The NMR spectrum (CDCl$_3$) showed absorptions at 1.53 (s, 3H), 1.72 (s, 3H), 3.47 (m, 2H), 4.5 (s, 1H), 4.6 (m, 1H) and 4.8 (m, 2H) ppm.

EXAMPLE 26

4-Nitrobenzyl Penicillanate 1,1-Dioxide

A solution of 4-nitrobenzyl penicillanate in chloroform was cooled to about 15° C. and 1 equivalent of 3-chloroperbenzoic acid was added. The reaction mixture was stirred for 20 minutes. Examination of the reaction mixture at this point by nuclear magnetic resonance spectroscopy revealed that it contained 4-nitrobenzyl penicillanate 1-oxide. A further 1 equivalent of 3-chloroperbenzoic acid was added and the reaction mixture was stirred for 4 hours. At this point a further 1 equivalent of 3-chloroperbenzoic acid was added and the reaction mixture was stirred overnight. The solvent was removed by evaporation, and the residue was partitioned between ethyl acetate and water at pH 8.5. The ethyl acetate layer was separated, washed with water, dried and evaporated to give the crude product. The crude product was purified by chromatography on silica gel, eluting with at 1:4 mixture of ethyl acetate/chloroform.

The NMR spectrum of the product (CDCl$_3$) showed absorptions at 1.35 (s, 3H), 1.58 (s, 3H), 3.45 (m, 2H), 4.42 (s, 1H), 4.58 (m, 1H), 5.30 (s, 2H) and 7.83 (q, 4H) ppm.

EXAMPLE 27

Penicillanic Acid 1,1-Dioxide

To 0.54 g. of 4-nitrobenzyl penicillanate 1,1-dioxide in 30 ml. of methanol and 10 ml. of ethyl acetate was added 0.54 g. of 10% palladium-on-carbon. The mixture was then shaken under an atmosphere of hydrogen at a pressure of about 50 psig. until hydrogen uptake ceased. The reaction mixture was filtered, and the solvent removed by evaporation. The residue was partitioned between ethyl acetate and water at pH 8.5, and the water layer was removed. Fresh ethyl acetate was added and the pH was adjusted to 1.5. The ethyl acetate layer was removed, washed with water and dried, and then it was evaporated in vacuo. This afforded 0.168 g. of the title compound as a crystalline solid.

EXAMPLE 28

Penicillanic Acid 1,1-Dioxide

A stirred solution of 512 mg. of 4-nitrobenzyl penicillanate 1,1-dioxide in a mixture of 5 ml. of acetonitrile and 5 ml. of water was cooled to 0° C. and then a solution of 484 mg. of sodium dithionite in 1.4 ml. of 1.0 N sodium hydroxide was added portionwise over several minutes. The reaction mixture was stirred for an additional 5 minutes and then it was diluted with ethyl acetate and water at pH 8.5. The ethyl acetate layer was removed and evaporated in vacuo giving 300 mg. of starting material. Fresh ethyl acetate was added to the aqueous phase and the pH was adjusted to 1.5. The ethyl acetate was removed, dried and evaporated in vacuo giving 50 mg. of the title compound.

EXAMPLE 29

1-Methyl-1-(acetoxy)ethyl Penicillanate 1,1-Dioxide

To 2.33 g. of penicillanic acid 1,1-dioxide in 5 ml. of N,N-dimethylformamide was added 1.9 ml. of ethyldiisopropylamine, followed by the dropwise addition of 1.37 g. of 1-methyl-1-(acetoxy)ethyl chloride, at ca 20° C. The mixture was stirred at ambient temperature overnight and then the mixture was diluted with ethyl acetate and with water. The layers were separated and the ethyl acetate layer was washed with water at pH 9. The ethyl acetate solution was then dried (Na$_2$SO$_4$) and evaporated in vacuo leaving 1.65 g. of crude product as an oil. The oil solidified on standing in the refrigerator, and it was then recrystallized from a mixture of chloroform and ether giving material having a melting point of 90°–92° C.

The NMR spectrum of the crude product (CDCl$_3$) showed absorptions at 1.5 (s, 3H), 1.62 (s, 3H), 1.85 (s, 3H), 1.93 (s, 3H), 2.07 (s, 3H), 3.43 (m, 2H), 4.3 (s, 1H) and 4.57 (m, 1H) ppm.

EXAMPLE 30

The procedure of Example 29 is repeated, except that the 1-methyl-1-(acetoxy)ethyl chloride is replaced by the appropriate 1-methyl-1-(alkanoyloxy)ethyl chloride, to produce the following compounds:

1-methyl-1-(propionyloxy)ethyl penicillanate 1,1-dioxide, 1-methyl-1-(pivaloyloxy)ethyl penicillanate 1,1-dioxide and 1-methyl-1-(hexanoyloxy)ethyl penicillanic acid 1,1-dioxide, respectively.

EXAMPLE 31

Penicillanic Acid 1,1-Dioxide

To a stirred solution of 1.78 g. of penicillanic acid in water, at pH 7.5, was added 1.46 ml. of 40% peracetic acid, followed by an additional 2.94 ml. of 40% peracetic acid 30 minutes later. The reaction mixture was stirred for 3 days at room temperature and then it was diluted with ethyl acetate and water. Solid sodium bisulfite was added to decompose excess peracid, and then the pH was adjusted to 1.5. The ethyl acetate layer was removed, dried (Na$_2$SO$_4$) and evaporated in vacuo. The residue was a 3:2 mixture of penicillanic acid 1,1-dioxide and penicillanic acid 1-oxide.

EXAMPLE 32

Pivaloyloxymethyl Penicillanate 1,1-Dioxide

A stirred solution of 595 mg. of pivaloyloxymethyl penicillanate 1-oxide in 5 ml. of ethyl acetate was cooled to ca −15° C., and 5 mg. of manganic acetylacetonate was added. To the dark brown mixture thus obtained was added, during several minutes, 0.89 ml. of 40% peracetic acid in small amounts over several minutes. After 40 minutes the cooling bath was removed, and the mixture was stirred at ambient temperature for 3 days. The mixture was diluted with ethyl acetate and water at pH 8.5, and the ethyl acetate layer was removed, dried and evaporated in vacuo. This afforded 178 mg. of material which was shown by NMR spectroscopy to be a mixture of pivaloyoxymethyl penicillanate 1,1-dioxide and pivaloyloxymethyl penicillanate 1-oxide.

The above material was redissolved in ethyl acetate and reoxidized using 0.9 ml. of peracetic acid and 5 mg. of manganic acetylacetonate, as described above, using a reaction time of 16 hours. The reaction mixture was worked up as described above. This afforded 186 mg. of pivaloyloxymethyl penicillanate 1,1-dioxide.

EXAMPLE 33

N-(Ethoxycarbonyl)aminomethyl Penicillanate 1,1-Dioxide

To 615 mg. (2.41 mmole) of penicillanic acid 1,1-dioxide in 3 ml. of N,N-dimethylformamide is added 215 mg. (2.50 mmole) of diisopropylethylamine, followed by 350 mg. (2.54 mmole) of N-(ethoxycarbonyl)aminomethyl chloride and 20 mg. of sodium iodide. The reaction mixture is stirred for 24 hours at ambient temperature, and then it is diluted with ethyl acetate and 10% aqueous sodium bicarbonate solution. The ethyl acetate layer is removed and then it is washed with water. The ethyl acetate solution is dried using anhydrous sodium sulfate, and evaporated in vacuo giving the title compound.

EXAMPLE 34

The procedure of Example 33 is repeated, except that the N-(ethoxycarbonyl)aminomethyl chloride is replaced by an equimolar amount of N-(methoxycarbonyl)aminomethyl chloride, N-(isobutyloxycarbonyl)aminomethyl chloride, N-(hexyloxycarbonyl)aminomethyl chloride, 1-(N-[methoxycarbonyl]amino)ethyl chloride and 1-(N-[hexyloxycarbonyl]amino)ethyl chloride, respectively.

This affords:

N-(methoxycarbonyl)aminomethyl penicillanate, 1,1-dioxide,

N-(isobutyloxycarbonyl)aminomethyl penicillanate 1,1-dioxide,

N-(hexyloxycarbonyl)aminomethyl penicillanate 1,1-dioxide, 1-(N-[methoxycarbonyl]amino)ethyl penicillanate 1,1-dioxide and 1-(N-[hexyloxycarbonyl]amino)ethyl penicillanate 1,1-dioxide, respectively.

EXAMPLE 35

Penicillanic Acid 1,1-Dioxide

To 100 ml. of water was added 9.4 g. of 6-alpha-bromopenicillanic acid 1,1-dioxide, at 22° C., followed by sufficient 4 N sodium hydroxide solution to achieve a stable pH of 7.3. To the resulting solution was added 2.25 g. of 5% palladium-on-carbon followed by 6.9 g. of dipotassium phosphate trihydrate. This mixture was then shaken under an atmosphere of hydrogen at a pressure varying from 3.5 to 1.8 kg/cm$^2$. When hydrogen uptake ceased, the solids were removed by filtration, and the aqueous solution was covered with 100 ml. of ethyl acetate. The pH was slowly lowered from 5.0 to 1.5 with 6 N-hydrochloric acid. The layers were separated, and the aqueous phase was extracted with further ethyl acetate. The combined ethyl acetate layers were washed with brine, dried using anhydrous magnesium sulfate and evaporated in vacuo. The residue was triturated under ether and then the solid material was collected by filtration. This afforded 4.5 g. (65% yield) of the title compound.

Analysis: Calcd. for $C_8H_{11}NO_5S$: C, 41.20; H, 4.75; N, 6.00; S, 13.75%. Found: C, 41.16; H, 4.81; N, 6.11; S, 13.51%.

EXAMPLE 36

Penicillanic Acid 1,1-Dioxide

The ethyl acetate solution of 6,6-dibromopenicillanic acid 1,1-dioxide from Preparation K was combined with 705 ml. of saturated sodium bicarbonate solution and 8.88 g. of 5% palladium-on-carbon catalyst. The mixture was shaken under an atmosphere of hydrogen, at a pressure of about 5 kg/cm$^2$ for about 1 hour. The catalyst was removed by filtration and the pH of the aqueous phase of the filtrate was adjusted to 1.2 with 6 N-hydrochloric acid. The aqueous phase was saturated with sodium chloride. The layers were separated and the aqueous phase was extracted with further ethyl acetate (3×200 ml.). The combined ethyl acetate solutions were dried (MgSO$_4$) and evaporated in vacuo to afford 33.5 g. (58% yield from 6-aminopenicillanic acid) of penicillanic acid 1,1-dioxide. This product was dissolved in 600 ml. of ethyl acetate, the solution was decolorized using activated carbon and the solvent was removed by evaporation in vacuo. The product was washed with hexane. This afforded 31.0 g. of pure product.

Example 37

Effect of Penicillanic Acid 1,1-Dioxide on the Antibacterial Activity of 7-(D-2[4-ethylpiperazine-2,3-dione-1-carboxamido]-2-[4-hydroxyphenyl]acetamido)-3-([1-methyl-5-tetrazolyl]thiomethyl)-3-desacetoxymethylcephalosporanic Acid The minimum inhibitory concentrations (MIC's) of penicillanic acid 1,1-dioxide (PA 1,1-dioxide) alone and 7-(D-2-[4-ethylpiperazine-2,3-dione-1-carboxamido]-2-[4-hydroxyphenyl]acetamido)-3-([1-methyl-5-tetrazolyl]thiomethyl)-3-desacetoxymethylcephalosporanic acid (T-1551) alone, against 30 strains of resistant *Escherichia coli*, were measured. These MIC's were then compared with the MIC values obtained with a combination of the two compounds. The results were as follows:

TABLE VI

| Micro-organism | No. of strains | Mode MIC of T-1551 alone | Mode MIC of PA 1,1-Dioxide alone | Mode MIC's of T-1551 & PA 1,1-Dioxide in Combination | |
|---|---|---|---|---|---|
| | | | | T-1551 | PA 1,1-Dioxide |
| *Escherichia coli* | 30 | 100 | 50 | 1.56 | 1.56 |

The MIC's were measured using the method recommended by the International Collaborative Study on Antibiotic Sensitivity Testing (Ericcson and Sherris, *Acta. Pathologica et Microbiologica* Scandivav, Supp. 217, Section B, 64–68 [1971]), which employed brain heart infusion agar and the inocular replicating device. Overnight growth tubes were diluted 10-fold for use as the standard inoculum. Twelve two-fold dilutions of the test compound were employed with initial concentration of the test drug being 200 mcg/ml. Single colonies were disregarded when reading plates after 18 hours at 37° C. The MIC of the test compound is accepted as the lowest concentration of compound capable of producing complete inhibition of growth as judged by the naked eye. The MIC's of combinations were measured using the method described by Barry and Sabath in "Manual of Clinical Microbiology", edited by Lenette, Spaulding and Truant, 2nd edition, 1974, American Society for Microbiology.

PREPARATION A

6,6-Dibromopenicillanic Acid 1α-Oxide

The title compound is prepared by oxidation of 6,6-dibromopenicillanic acid with 1 equivalent of 3-chloroperbenzoic acid in tetrahydrofuran at 0°–25° C. for ca. 1 hour, according to the procedure of Harrison et al., *Journal of the Chemical Society* (London) Perkin I, 1772 (1976).

PREPARATION B

Benzyl 6,6-Dibromopenicillanate

To a solution of 54 g. (0.165 mole) of 6,6-dibromopenicillanic acid in 350 ml. of N,N-dimethylacetamide was added 22.9 ml. (0.165 mole) of triethylamine and the solution was stirred for 40 minutes. Benzyl bromide (19.6 ml., 0.165 mole) was added and the resulting mixture was stirred at room temperature for 48 hours. The precipitated triethylamine hydrobromide was filtered off, and the filtrate was added to 1,500 ml. of ice-water, adjusted to pH 2. The mixture was extracted with ether, and the extracts were washed successively with saturated sodium bicarbonate, water and brine. The dried ($MgSO_4$) ether solution was evaporated in vacuo to give an off-white solid, which was recrystallized from isopropanol. This afforded 70.0 g. (95% yield) of the title compound m.p. 75°–76° C. The IR spectrum (KBr disc) showed absorptions at 1795 and 1740 $cm^{-1}$. The NMR spectrum ($CDCl_3$) showed absorptions at 1.53 (s, 3H), 1.58 (s, 3H), 4.50 (s, 1H), 5.13 (s, 2H), 5.72 (s, 1H) and 7.37 (s, 5H) ppm.

PREPARATION C

Benzyl 6,6-Dibromopenicillanate 1α-Oxide

To a stirred solution of 13.4 g. (0.03 mole) of benzyl 6,6-dibromopenicillanate in 200 ml. of dichloromethane was added a solution of 6.12 g. (0.03 mole) of 3-chloroperbenzoic acid in 100 ml. of dichloromethane, at ca. 0° C. Stirring was continued for 1.5 hours at ca. 0° C. and then the reaction mixture was filtered. The filtrate was washed successively with 5% sodium bicarbonate and water, and then it was dried ($Na_2SO_4$). Removal of the solvent by evaporation in vacuo gave 12.5 g. of the title product as an oil. The oil was induced to solidify by trituration under ether. Filtration then afforded 10.5 g. of benzyl 6,6-dibromopenicillanate 1α-oxide as a solid. The IR spectrum ($CHCl_3$) showed absorptions at 1800 and 1750 $cm^{-1}$. The NMR spectrum of the product ($CDCl_3$) showed absorptions at 1.3 (s, 3H), 1.5 (s, 3H), 4.5 (s, 1H) 5.18 (s, 2H), 5.2 (s, 1H) and 7.3 (s, 5H) ppm.

PREPARATION D

4-Nitrobenzyl Penicillanate

Reaction of the triethylamine salt of penicillanic acid with 4-nitrobenzyl bromide; according to the procedure of Preparation B, affords 4-nitrobenzyl penicillanate.

PREPARATION E

2,2,2-Trichloroethyl Penicillanate

To 403 mg. of penicillanic acid in 10 ml. of dichloromethane was added 25 mg. of diisopropylcarbodiimide followed by 0.19 ml. of 2,2,2-trichloroethanol. The mixture was stirred overnight and then the solvent was removed by evaporation in vacuo. The crude product was purified by column chromatography using silica gel as the adsorbent and chloroform as the eluant.

PREPARATION F

3-Phthalidyl Penicillanate

To a solution of 506 mg. of penicillanic acid in 2 ml. of N,N-dimethylformamide was added 0.476 ml. of diisopropylethylamine followed by 536 mg. of 3-phthalidyl bromide. The mixture was stirred overnight and then it was diluted with ethyl acetate and water. The pH was adjusted to 3.0 and the layers were separated. The organic layer was washed with water, and then with water at pH 8.0, and then it was dried using anhydroous sodium sulfate. The dried ethyl acetate solution was evaporated in vacuo giving 713 mg. of the title ester as an oil. The NMR spectrum ($CDCl_3$) showed absorptions at 1.62 (m, 6H), 3.3 (m, 2H), 4.52 (s, 1H), 5.23 (m, 1H) and 7.63 (m, 5H).

PREPARATION G

Pivaloyloxymethyl Penicillanate

To 3.588 g. of 6,6-dibromopenicillanic acid in 10 ml. of N,N-dimethylformamide was added 1.8 ml. of diisopropylethylamine, followed by 1.40 ml. of chloromethyl pivalate. The mixture was stirred overnight and then it was diluted with ethyl acetate and water. The organic layer was removed and washed succesively with water at pH 3.0 and water at pH 8.0. The ethyl acetate solution was dried ($Na_2SO_4$) and then evaporated in vacuo to give pivaloyloxymethyl 6,6-dibromopenicillanate as an amber oil (3.1 g.) which slowly crystallized.

The above ester was dissolved in 100 ml. of methanol, and then 3.1 g. of 10% palladium-on-carbon and 1.31 g. of potassium bicarbonate in 20 ml. of water were added. The mixture was shaken under hydrogen at atmospheric pressure until hydrogen uptake ceased. The reaction mixture was filtered and the methanol was removed by evaporation in vacuo. The residue was partitioned between water and ethyl acetate at pH 8, and then the organic layer was removed. The latter was dried ($Na_2SO_4$) and evaporated in vacuo to give 1.25 g. of the title compound. The NMR spectrum ($CDCl_3$) showed absorptions at 1.23 (s, 9H), 1.5 (s, 3H), 1.67 (s, 3H), 3.28 (m, 2H), 4.45 (s, 1H), 5.25 (m, 1H) and 5.78 (m, 2H) ppm.

PREPARATION H

4-Nitrobenzyl Penicillanate

To a stirred solution of 2.14 g. of penicillanic acid and 2.01 ml. of ethyldiisopropylamine in 10 ml. of N,N-dimethylformamide was added dropwise 2.36 g. of 4-nitrobenzyl bromie, at ca. 20° C. The mixture was stirred at ambient temperature overnight, and then it was diluted with ethyl acetate and water. The layers were separated and the ethyl acetate layer was washed with water at pH 2.5, followed by water at pH 8.5. The ethyl acetate solution was then dried ($Na_2SO_4$) and evaporated in vacuo leaving 3.36 g. of the title compound.

The NMR spectrum of the product (in $CDCl_3$) showed absorptions at 1.45 (s, 3H), 1.68 (s, 3H), 3.32 (m, 2H), 4.50 (s, 1H), 5.23 (m, 1H), 5.25 (s, 2H) and 7.85 (q, 4H) ppm.

PREPARATION I

6-alpha-Bromopenicillanic Acid 1,1-dioxide

To a stirred mixture of 560 ml. of water, 300 ml. of dichloromethane and 56.0 g. of 6-alpha-bromopenicillanic acid was added 4 N sodium hydroxide solution until a stable pH of 7.2 was achieved. This required 55 ml. of sodium hydroxide. The mixture was stirred at pH 7.2 for 10 minutes and then it was filtered. The layers were separated and the organic phase was discarded. The aqueous phase was then poured rapidly, with stirring, into an oxidizing mixture which had been prepared as follows.

In a 3 liter flask was mixed 63.2 g. of potassium permanganate, 1,000 ml. of water and 48.0 g. of acetic acid. This mixture was stirred for 15 minutes at 20° C. and then it was cooled to 0° C.

After the 6-alpha-bromopenicillanic acid solution had been added to the oxidizing mixture, a cooling bath at −15° C. was maintained around the reaction mixture. The internal temperature rose to 15° C. and then fell to 5° C. over a 20 minute period. At this point, 30.0 g. of sodium metabisulfite was added with stirring over a 10 minute period at about 10° C. After a further 15 minutes, the mixture was filtered, and the pH of the filtrate was lowered to 1.2 by the addition of 170 ml. of 6 N hydrochloric acid. The aqueous phase was extracted with chloroform, and then with ethyl acetate. Both the chloroform extracts and the ethyl acetate extracts were dried using anhydrous magnesium sulfate and then they were evaporated in vacuo. The chloroform solution afforded 10.0 g. (16% yield) of the title compound. The ethyl acetate solution afforded 57 g. of an oil, which was triturated under hexane. A white solid appeared. It was filtered off, giving 41.5 g. (66% yield) of the title compound, mp 134° C. (dec.).

PREPARATION J

6,6-Dibromopenicillanic Acid

To 500 ml. of dichloromethane cooled to 5° C. was added 119.9 g. of bromine, 200 ml. of 2.5 N sulfuric acid and 34.5 g. of sodium nitrite. To this stirred mixture was then added 54.0 g.of 6-aminopenicillanic acid, portionwise over 30 minutes, with the temperature maintained from 4° to 10° C. Stirring was continued for 30 minutes at 5° C., and then 410 ml. of a 1.0 M solution of sodium bisulfite was added dropwise at 5° to 10° C. during 20 minutes. The layers were separated and the aqueous layer was extracted twice with 150 ml. of dichloromethane. The original dichloromethane layer was combined with the two extracts to give a solution of 6,6-dibromopenicillanic acid. This solution was used directly in Preparation K.

PREPARATION K

6,6-Dibromopenicillanic Acid 1,1-Dioxide

To the dichloromethane solution of 6,6-dibromopenicillanic acid from Preparation J was added 300 ml. of water, followed by the dropwise addition over a period of 30 minutes of 105 ml. of 3 N sodium hydroxide. The pH stabilized at 7.0. The aqueous layer was removed and the organic layer was extracted with water (2×100 ml.). To the combined aqueous solutions was added, at −5° C., a premixed solution prepared from 59.25 g. of potassium permanganate, 18 ml. of concentrated phosphoric acid and 600 ml. of water, until the pink color of the permanganate persisted. The addition took 50 minutes and 500 ml. of oxidant were required. At this point, 500 ml. of ethyl acetate was added and then the pH was lowered to 1.23 by the addition of 105 ml. of 6 N hydrochloric acid. Then 250 ml. of 1 M sodium bisulfite was added during 10–15 minutes at ca. 10° C. During the addition of the sodium bisulfite solution, the pH was maintained at 1.25–1.35 using 6 N hydrochloric acid. The aqueous phase was saturated with sodium chloride and the two phases were separated. The aqueous solution was extracted with additional ethyl acetate (2×150 ml.) and the combined ethyl acetate solutions were washed with brine and dried (MgSO4). This afforded an ethyl acetate solution of 6,6-dibromopenicillanic acid 1,1-dioxide.

The 6,6-dibromopenicillanic acid 1,1-dioxide can be isolated by removal of the solvent in vacuo. A sample so isolated from an analgous preparation had a melting point of 201° C. (dec.). The NMR spectrum CDCl3/DMSO-d6) showed absorptions at 9.35 (s, 1H), 5.30 (S, 1H), 4.42 (s, 1H), 1.63 (s, 3H) and 1.50 (s, 3H) ppm. The IR spectrum (KBr disc) showed absorptions at 3846–2500, 1818, 1754, 1342 and 1250–1110 cm$^{-1}$.

What is claimed is:

1. A method of treating a bacterial infection in a mammal subject which comprises administering to said subject (A) 7-(D-2-[4-ethylpiperazin-2,3-dione-1-carboxamido]-2-[4-hydroxyphenyl]acetamide)-3-([1-methyl-5-tetrazolyl]thiomethyl)-3-desacetoxymethylcephalosporanic acid or a pharmaceutically-acceptable salt thereof and (B) a compound of the formula

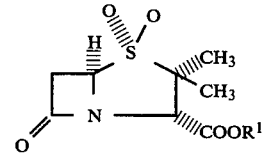

or a pharmaceutically-acceptable salt thereof, the weight ratio of (A) to (B) administered being in the range of from 1:6 to 6:1, the combined amounts of (A) and (B) administered constituting an antibacterially effective dosage and R1 being selected from the group consisting of hydrogen, alkanoyloxymethyl having from 3 to 8 carbon atoms, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N[alkoxycarbonyl]amino-ethyl having from 4 to 10 carbon atoms, 3-phthalidyl, 4-crotonolactonyl and gamma-butyrolactonyl-4-yl.

2. The method according to claim 1 wherein R$^1$ is hydrogen.

3. The method according to claim 1 wherein R$^1$ is pivaloyloxymethyl

4. The method according to claim 1 wherein R$^1$ is 1-(ethoxycarbonyloxy)ethyl.

5. A pharmaceutical composition useful for treating bacterial infections in mammals, which comprises 7-(D-2-[4-ethylpiperazin-2,3-dione-1-carboxamido]2-[4-hydroxyphenyl]acetamido)-3-([1-methyl-5-tetrazolyl]-thiomethyl)-3-desacetoxymethylcephalosporanic acid, or a pharmaceutically-acceptable salt thereof, and a compound of the formula or a pharmaceutically-acceptable base salt thereof, in a weight ratio in the range from about 1:6 to 6:1, wherein $R^1$ is selected from the group consisting of hydrogen, alkanoyloxymethyl having from 3 to 8 carbon atoms, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-[alkoxycarbonyl]amino)ethyl having from 4 to 10 carbon atoms, 3-phthalidyl, 4-crotonolactonyl and gamma-butyrolacton-4-yl.

6. A pharmaceutical composition according to claim 5 which further comprises a pharmaceutically-acceptable carrier wherein said carrier is present in an amount of from about 5 to about 80% by weight.

7. A pharmaceutial composition according to claim 6 wherein $R^1$ is hydrogen.

8. A pharmaceutical composition according to claim 5 wherein $R^1$ is pivaloyloxymthyl.

9. A pharmaceutical composition according to claim 6 wherein $R^1$ is 1-(ethoxycarbonyloxy)ethyl.

* * * * *

UNITED STATES PATENT OFFICE
CERTIFICATE OF CORRECTION

Patent No. 4,276,285               Dated June 30, 1981

Inventor(s) Wayne E. Barth

It is certified that error appears in the above-identified patent and that said Letters Patent are hereby corrected as shown below:

Title page opposite the heading [*] Notice: should read --The portion of the term of this patent subsequent to November 18, 1997, has been disclaimed.--

Title page, under "OTHER PUBLICATIONS", in the second entry, "1977" should read --1772--.

Title page, under "OTHER PUBLICATIONS", in the third entry, "73" should read --13-- and "1967" should read --1968--.

Title page, under "OTHER PUBLICATIONS" in the fifth entry, "B-Lactan" should read --β-Lactam-- and "Elka" should read --Elks--.

At column 2, line 40, that protion of the formula reading

" 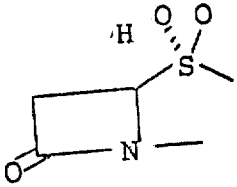 " should read -- 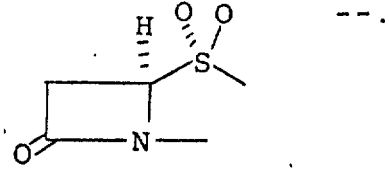 --.

UNITED STATES PATENT OFFICE
CERTIFICATE OF CORRECTION

Patent No. 4,276,285    Dated June 30, 1981

Inventor(s) Wayne E. Barth

It is certified that error appears in the above-identified patent and that said Letters Patent are hereby corrected as shown below:

At column 12, line 30, "carboxamidol" should read --carboxamido]--.

At column 12, lines 36 through 47, that portion of the formula reading

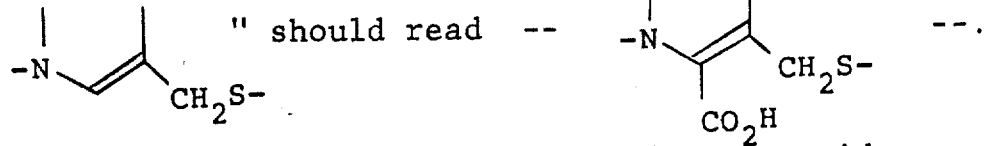

Column 30, line 28, "acetamide" should read --acetamido--.

Column 30, line 45, "$R_1$" should read --$R^1$--.

Claim 8, line 3 (column 32, line 15), "pivaloyloxymthyl" should read --pivaloyloxymethyl--.

Signed and Sealed this

Twenty-second Day of December 1981

|SEAL|

Attest:

GERALD J. MOSSINGHOFF

Attesting Officer    Commissioner of Patents and Trademarks